Aug 28, 1951 O. E. FELTEN Plant Pat. 1,033
STRAWBERRY PLANT
Filed Oct. 6, 1949
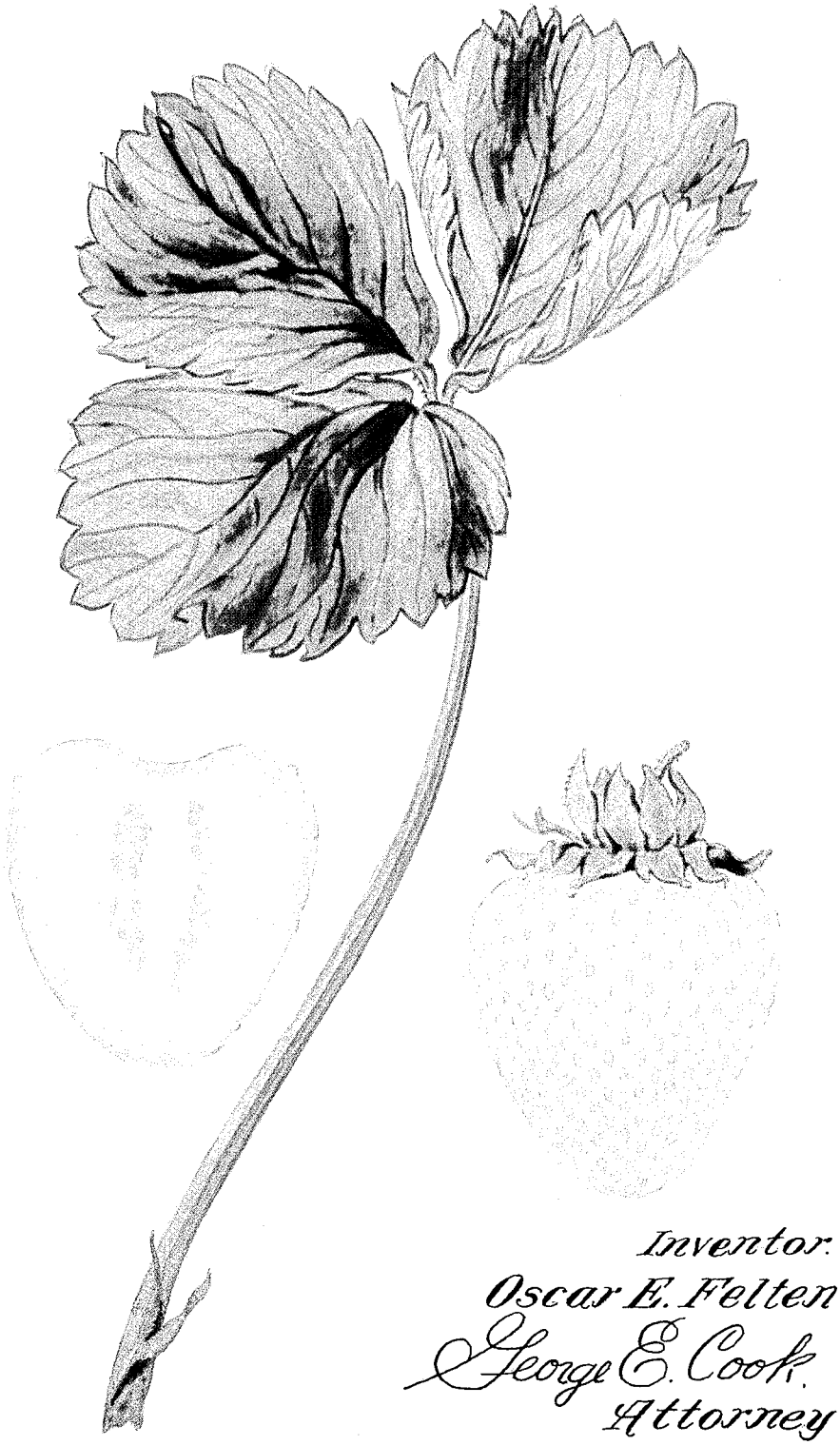
Inventor:
Oscar E. Felten
George E. Cook,
Attorney Patented Aug. 28, 1951

Plant Pat. 1,033

UNITED STATES PATENT OFFICE 1,033

STRAWBERRY PLANT

Oscar Earle Felten, East Merchantville, N. J.

Application October 6, 1949, Serial No. 119,781

1 Claim. (Cl. 47—62)

My present invention pertains to an improved variety of strawberry plant which originated as the result of definite breeding efforts made by me at my gardens in Merchantville, N. J. Its parents are Mildred Felten (Plant Patent 761) and an unnamed seedling originated by me.

The variety has been asexually reproduced by me at my gardens, both by means of runners and by division. Sufficient plants have been produced to enable us to try out the marketability of the fruit. The distinguishing features of the variety have proved to be permanent.

The accompanying illustrations show a leaf, a typical berry, and the cross-section of another berry, all in approximately their true colors.

In the following detailed description, color plate numbers refer to Ridgway's Color Standards and Nomenclature.

*The plant*

Type: Self-pollinizing.

Growth: Upright; healthy; at least as tall as the subject of Plant Patent No. 761. Plant becomes very large, producing a heavy crown. Runners are plentiful and heavy, making a good row of heavy plants. Beds up in masses. Does exceptionally well in heavy soil.

Disease resistance: Apparently very robust and healthy. No virus diseases have ever been seen, although a slight amount of leafspot may occur.

Production habit: Produces many large berries, those of the last of the season being as large as the earlier ones.

Maturity season: This is a June berry, coming into bearing a day or two later than Mildred Felton. It has an exceptionally long fruiting season—approximately three weeks, terminating about July 1st.

Foliage:

*Quantity.*—Plenty but not over-foliated. Tends to let the sun get to the berry for ripening.

*Texture.*—Heavy and substantial.

*Color.*—Approximately Spinach Green (Plate V) on the upper surface and considerably lighter on the under surface. Many of the older leaves are bronzed.

*Shape.*—Trifoliate, with leaflets almost round. Each leaflet is slightly cupped and the edge is scalloped rather than notched or serrated.

*Size.*—Terminal leaflet of a full-grown leaf is approximately 3¾ inches long by 3½ inches wide. Lateral leaflets are slightly smaller.

*Leaf stems or petioles.*—Tallest are approximately 9 inches in length. Approximately Lettuce Green (Plate V), with a considerable amount of bronzed overlay. Pedicels of the three leaflets are very short, making the leaflets almost sesile.

*Flowers*

Color: White.

Size: Large—about the size of those of Mildred Felten.

Flower and fruit stems: Slender, crisp, strong, tall. Very numerous in comparison to size of crown. Although tall, they come under the foliage, thus protecting the flowers from late frosts in the spring.

*Fruit*

Shape: Mostly conic, with a few of the early berries slightly shouldered. Very slightly grooved.

Size: Large size, which is maintained until the end of the bearing season. Berries measure up to 1¾ inches across, both transversely and vertically, with an average measurement of 1½ inches. Circumference in either direction measures up to 5 inches.

Skin:

*Aspect.*—Shiny and brilliant, covered with many bright yellow seeds giving a golden cast.

*Texture.*—Smooth, substantial enough to protect berry but not tough.

*Color.*—Approximately Peach Red (Plate I) at picking stage, which it retains for several days thereafter. Darkens to a deep red (almost Nopal Red) (Plate I) when kept for several days and allowed to become overripe.

Seeds: Many bright shiny yellow seeds, rather evenly distributed over the surface of the berry. Seeds are small and near the surface, protruding slightly, thus protecting the berry.

Flesh:

*Flavor.*—Tart but not sour, with a distinctive quality which seems somewhat pineapple-like. When one first bites into a berry, it seems sweet.

*Texture.*—Fine, melting, firm but not solid.

*Juiciness.*—Contains large quantity of juice.

*Core.*—Many of the larger berries have a core which is slightly more firm than the other flesh. This core is usually surrounded by a small hollow area.

*Color.*—Basic color of the flesh is approximately the same as the skin. Outlining the hollow area surrounding the core is a fine line of white, with lighter veins of white radiating from this line to the berry's edge.

*Comparison*

My new variety is more like the Mildred Felten (Plant Patent No. 761)—one of its parents—than any known variety. It differs from that variety, principally in the following points:

Individual plants of my new variety are less heavily foliated.

Color of the foliage is slightly lighter.

Foliage is more upright.

Runners are more numerous, making the reproduction of plants more plentiful.

Plants bed up more in masses.

Plant stands wet weather better.

Its maturity season extends later.

Is not quite as heavy a bearer.

Color of berry is lighter or more golden, and holds better.

Berries are firmer, with more protective seeds.

Berries have a distinctive flavor.

Berries are not quite so large but the size of berry holds up better through a longer picking season.

Calyx is larger and adheres much better.

Having thus disclosed my invention, I claim:

The new and improved variety of strawberry plant, substantially as herein disclosed, characterized particularly by its heavy production of runners and massed bedding; its sturdy, upright foliage and fruit stems; its vigorous growth and resistance to most diseases and to the usual destruction of wet weather; the great length of the bearing season with retention of size of berry throughout; the unusually good adherence of its large calyx; and its berries combining large size, bright red color, firmness of both flesh and skin, and pleasing rich distinctive flavor.

OSCAR EARLE FELTEN.

REFERENCES CITED

The following references are of record in the file of this patent:

UNITED STATES PATENTS

| Number | Name | Date |
|---|---|---|
| Pl. Pt. 46 | Cordrey et al. | Nov. 29, 1932 |
| Pl. Pt. 112 | Aiken | Nov. 20, 1934 |